United States Patent [19]

Atalla et al.

[11] 4,306,892
[45] Dec. 22, 1981

[54] DISPOSABLE AIR FRESHENING PACKET

[75] Inventors: Anwar A. Atalla, Glen Ellyn; Richard E. Swin, Sr., Indianhead Park, both of Ill.

[73] Assignee: TEC-AIR, Inc., Willow Springs, Ill.

[21] Appl. No.: 231,926

[22] Filed: Feb. 6, 1981

[51] Int. Cl.³ .............................................. B01D 46/00
[52] U.S. Cl. ........................................ 55/279; 55/504; 55/515; 55/516; 55/524; 422/4; 422/5; 422/123
[58] Field of Search .................. 55/279, 316, 387–389, 55/524, 516, 515, 384, 493, 504; 422/5, 4, 123; 210/498, 499

[56] References Cited

U.S. PATENT DOCUMENTS

| 1,737,532 | 11/1929 | Allen | 55/387 |
| 2,614,820 | 10/1952 | Boydjieff | 422/4 |
| 4,102,656 | 7/1978 | Koritz | 55/504 |
| 4,216,003 | 8/1980 | Diachak | 55/508 |

Primary Examiner—Bernard Nozick
Attorney, Agent, or Firm—August E. Roehrig, Jr.

[57] ABSTRACT

A disposable packet, containing an air freshening medium, and formed with securing elements such that the packet may be positioned and retained in an air stream for removing contaminants and offensive odors from the air and discharging a filtered scented fragrance.

8 Claims, 7 Drawing Figures

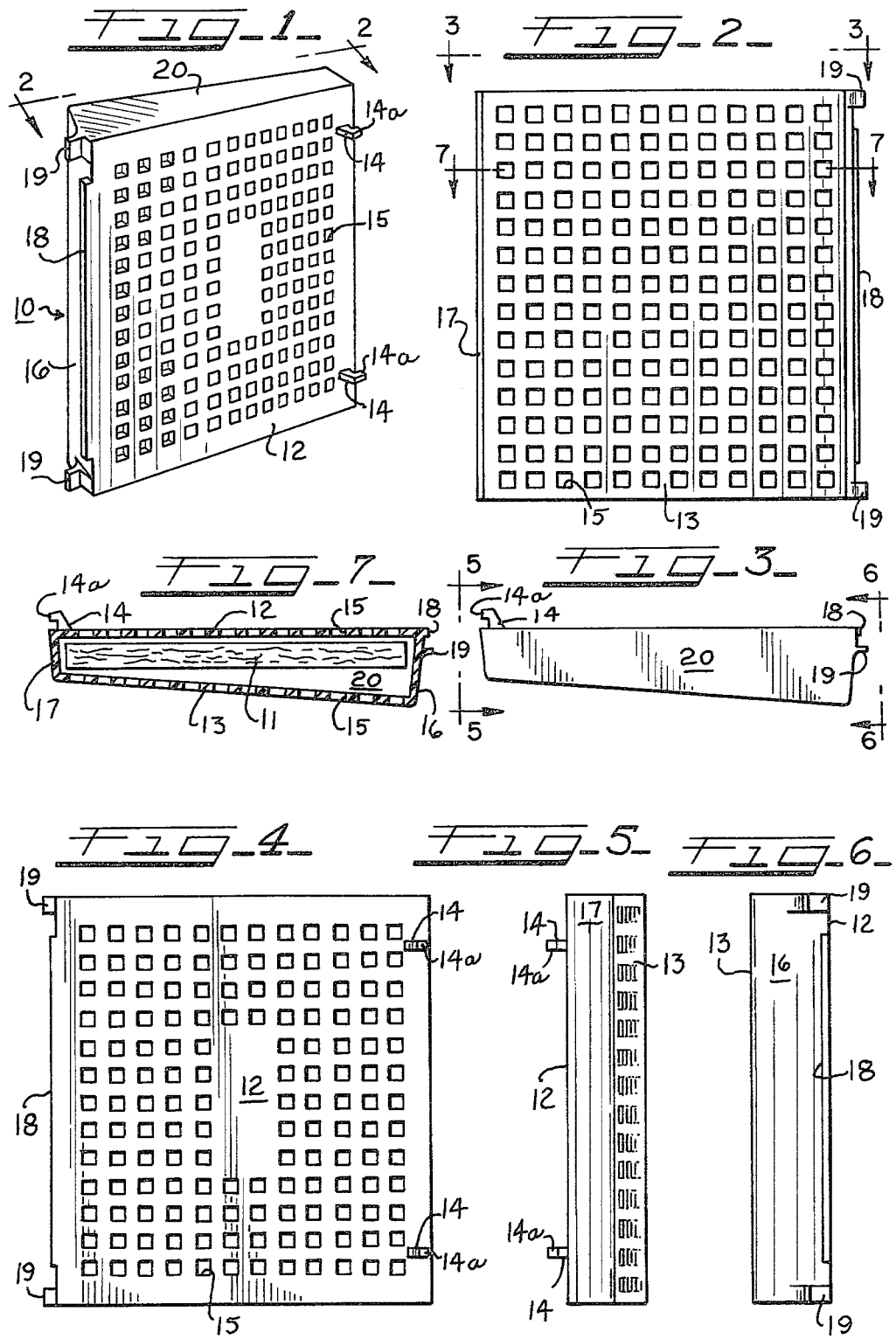

DISPOSABLE AIR FRESHENING PACKET

BACKGROUND OF THE INVENTION

This invention relates in general to disposable air fresheners and, in particular, to a disposable packet which contains a quantity of air freshening material. More specifically, but without restriction to the particular use which is shown and described, this invention relates to a disposable packet containing an air freshening material which may be positioned and retained in an air stream until such time as the air freshening material is expended and the packet is then replaced.

Various types of devices have been utilized to treat the air within a confined enclosure or room. Many of such devices are static in that a deodorizing material is exposed to the ambient conditions within a room and through sublimation a solid deodorizing material is transformed into vapor which provides a pleasant scent for masking odors. Other systems utilize a filter to recirculate the air within a room or enclosure through a filter medium to remove particles such as pollen, dust or the like. While such deodorizing or filtering devices help to alleviate the problem of offensive odors or irritants in the air, they are generally of limited efficiency or expensive.

SUMMARY OF THE INVENTION

It is, therefore, an object of this invention to improve air freshening.

Another object of this invention is to combine a deodorizing and filtering system in a disposable air freshening packet.

A further object of this invention is to inexpensively freshen the air within a room or enclosure by filtering contaminants from the air, removing offensive odors, and discharging a pleasant scent or fragrance thereinto.

These and other objects are attained in accordance with the present invention wherein there is provided a disposable packet, containing an air freshening medium, and formed with securing elements such that the packet may be positioned and retained in an air stream for removing contaminants and offensive odors from the air and discharging a filtered scented fragrance.

DESCRIPTION OF THE DRAWINGS

Further objects of the invention together with additional features contributing thereto and advantages accruing therefrom will be apparent from the following description of a preferred embodiment of the invention which is shown in the accompanying drawings with like reference numerals indicating corresponding parts throughout, wherein:

FIG. 1 is a frontal perspective view of an air freshening packet constructed in accordance with the invention;

FIG. 2 is a frontal elevation view of the air freshening packet shown in FIG. 1 taken in the direction of lines 2—2;

FIG. 3 is a top plan view of the air freshening packet of FIG. 2 taken in the direction of lines 3—3;

FIG. 4 is a rear elevation view of the air freshening packet shown in FIG. 1 from the side opposite that shown in FIG. 2;

FIG. 5 is an end view of the air freshening packet shown in FIG. 3 taken in the direction of lines 5—5;

FIG. 6 is an end profile view of the air freshening packet shown in FIG. 3 taken in the direction of lines 6—6; and FIG. 7 is a cross-sectional view of the air freshening packet shown in FIG. 2 taken in the direction of lines 7—7.

DESCRIPTION OF A PREFERRED EMBODIMENT

Referring now to FIGS. 1 and 7, there is shown a disposable air freshening packet 10 containing an air filtering/deodorizing medium 11 enclosed within the packet 10 and positioned between two perforated walls 12 and 13. A pair of lock tabs 14 are carried on an outer face of wall 12 for engagement with a suitable mating element (not shown) to hold the packet 10 in the path of an air flow so that the air will pass through a plurality of square perforations 15 formed in the wall 12, passing through the air freshening medium 11 to emerge through the perforations 15 of the opposite wall 13 which is shown in FIG. 2. While for convenience of illustration the air flow is described as entering through wall 12 and exiting through wall 13, it is to be understood that the path of air flow can be in the opposite direction. The wall 13, opposite to wall 12, is formed as a smooth perforated wall with no tabs or other securing structure extending therefrom as best shown in FIGS. 2, 3 and 7.

The two perforated walls 12 and 13 are spaced one from the other by two side walls 16 and 17. End walls 20, the same on the top and bottom, complete the defined enclosure. The side wall 16 extends a greater length than the side wall 17 to space the perforated walls 12 and 13 a greater distance apart at their edges joining side wall 16 than where their edges join side wall 17 creating a tapered configuration for the packet 10.

As best shown in FIG. 7, the air freshening medium 11, preferably a felt pad saturated in a fragrant oil, is sealed within the packet 10 between the two perforated walls 12 and 13. In this manner, air passing through the rectangular apertures or perforations 15 in walls 12 or 13, will pass through the air freshening medium 11 to exit from the opposed perforated wall. The air freshening medium 11 will thereby filter contaminants from the air, such as dust or pollen, due to the mechanical action of the air passing through the filtering medium 11, and entrap odors from the air. The air passed through the freshening medium 11 will carry a fragrant scent which will depend upon the particular scented medium or fragrant oil in which the pad is saturated.

Since the packet 10 is disposable, and for effective operation must be positioned in an air flow path, the packet 10 includes suitable attaching devices so that it may be retained in a position against the air flow to which it is exposed. To this end the lock tabs or hooks 14 extend outwardly from the perforated wall 12, normal to the surface thereof, a predetermined distance from the surface and terminate to form a hook-like or lip portion 14a which extends parallel to the wall 12. In this manner the lock tabs 14 form a hook-like or lip projection extending outwardly from the surface of wall 12 to engage a suitable retaining element (not shown) for holding one side of the disposable packet 10 in a secured position against an air flow.

The side or edge of perforated wall 12 opposite to that carrying the lock tabs 14 is formed with a lip 18 which extends outwardly beyond the juncture of the perforated wall 12 with side wall 16 but, as best shown in FIGS. 1, 2, 4 and 6, perferably does not extend throughout the entire length of the juncture with side wall 16, although it may be so formed. A pair of bearing tabs 19 are carried on the side wall 16, in adjacent spaced relation to the lip 18, and extend outwardly from the side wall 16 to form another portion of a support, which in combination with lip 18, is used for securing this side of the packet 10 in a position against the air flow to which it is exposed. While the lip 18 is shown formed on perforated wall 18, at the juncture with side wall 16, the lip 18 may also be formed on the side wall 16 at the juncture with perforated wall 12. The lip 18 and bearing tabs 19 may be positioned on opposite sides of an element (not shown) which would extend therebetween to thereby position and secure the packet in a path of air flow.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A disposable air freshening packet for treating air comprising
    a first perforated wall defining a first surface area having perforations extending through substantially all of the first surface area defined thereby,
    a second perforated wall defining a second surface area having perforations extending through substantially all of the second surface area defined thereby,
    a first side wall and a second side wall each joined to said first and second perforated walls for positioning said perforated walls in spaced relationship to each other to define a portion of an enclosure formed therebetween,
    wall means joined to said first and second perforated walls and said first and second side walls for completing said enclosure,
    air treating means carried within said enclosure for freshening air passed therethrough,
    a first retaining means comprising a hook-like projection extending outwardly adjacent a juncture of said first perforated wall and one of said side walls, and having a free end extending outward from said juncture for securing the packet in a stable position, and
    a second retaining means comprising a lip and bearing tab carried adjacent a juncture of said first perforated wall and the other of said side walls,
    said lip and said bearing tab being spaced from each other and extending outwardly from said juncture of said first perforated wall and said other of said side walls for securing the packet in a stable position.

2. The apparatus of claim 1 wherein one of said side walls is of a greater dimension than the other of said side walls so that said first and second perforated walls converge toward each other.

3. The apparatus of claim 1 wherein said first retaining means is carried on said first perforated wall,
    said bearing tabs are carried on one of said side walls,
    said lip is carried by said side wall carrying said bearing tabs and said first perforated wall.

4. The apparatus of claim 1 wherein said first retaining means is carried on said first perforated wall.

5. The apparatus of claim 1 wherein said bearing tabs are carried on one of said side walls.

6. The apparatus of claim 5 wherein said lip is carried on said perforated wall and one of said side walls.

7. The apparatus of claim 5 wherein said lip is carried on said perforated wall.

8. The apparatus of claim 5 wherein said lip is carried on one of said side walls.

* * * * *